(12) United States Patent
Müller et al.

(10) Patent No.: US 8,393,556 B2
(45) Date of Patent: Mar. 12, 2013

(54) PREPARATION OF NANOSCALAR UV ABSORBERS

(75) Inventors: Stefan Müller, Weil am Rhein (DE); Bernd Herzog, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 249 days.

(21) Appl. No.: 12/664,429

(22) PCT Filed: Jun. 27, 2008

(86) PCT No.: PCT/EP2008/058250
§ 371 (c)(1),
(2), (4) Date: Apr. 19, 2010

(87) PCT Pub. No.: WO2009/003934
PCT Pub. Date: Jan. 8, 2009

(65) Prior Publication Data
US 2010/0193614 A1    Aug. 5, 2010

(30) Foreign Application Priority Data

Jul. 4, 2007   (EP) ..................................... 07111752

(51) Int. Cl.
*B02C 15/00*   (2006.01)
(52) U.S. Cl. ........................................................ 241/16

(58) Field of Classification Search ...................... 241/16
See application file for complete search history.

(56) References Cited

U.S. PATENT DOCUMENTS

| 5,980,872 | A | 11/1999 | Luther et al. |
| 7,311,897 | B2 * | 12/2007 | Ehlis et al. ...................... 424/59 |
| 2002/0172713 | A1 | 11/2002 | Einziger et al. |
| 2003/0096011 | A1 | 5/2003 | Tracy et al. |
| 2004/0191191 | A1 | 9/2004 | Ehlis |

FOREIGN PATENT DOCUMENTS

| WO | 9703643 A | 2/1997 |
| WO | 0072830 A | 7/2000 |
| WO | 02076420 A | 10/2002 |

* cited by examiner

*Primary Examiner* — Mark Rosenbaum
(74) *Attorney, Agent, or Firm* — Tyler A. Stevenson

(57) ABSTRACT

Disclosed is a method of preparing a composition, comprising a micronized insoluble organic UV absorber, which method comprises grinding the insoluble organic UV absorber, in coarse particle form, in a grinding apparatus comprising yttrium-stabilized zirconium oxide grinding beads, in the presence of alkyl polyglucoside having the formula $C_nH_{2n+1}O(C_6H_{10}O_5)_xH$, in which n is an integer ranging from 8 to 16 and x is the mean polymerisation level of the glucoside moiety $(C_6H_{10}O_5)$ and ranges from 1.4 to 1.6, or an ester thereof and in the presence of an antifoam agent as dispersingagent auxiliary.

15 Claims, No Drawings

PREPARATION OF NANOSCALAR UV ABSORBERS

The present invention relates to a method for producing new formulations of UV absorbers and to their use in sunscreen compositions which, in turn, are useful, in particular, for the protection of human skin.

It has long been known that prolonged exposure to that UV radiation which reaches the surface of the earth can lead to the formation of erythemas or light dermatoses, as well as to an increased incidence of skin cancers or accelerated skin aging.

Various sunscreen formulations have been proposed which include a material which is intended to counteract UV radiation, thereby inhibiting the said undesired effects on the skin.

A great number of compounds has been proposed for use as UV protectants in sunscreen formulations, especially soluble organic UV absorbers and insoluble micronized inorganic compounds, in particular zinc oxide and titanium dioxide.

The high specific weight of insoluble inorganic compounds, such as zinc oxide and titanium dioxide leads to a reduced stability of formulations containing them. Moreover, such inorganic compounds have been claimed to generate toxic radicals under the influence of light ("Redox Mechanisms in Heterogeneous Photocatalysis", Serpone et al, Electrochemistry in Colloids and Dispersions, Editors Mackay and Texter, VCH Publishers Inc., New York 1992).

Micronised, insoluble organic UV absorbers, when used in sunscreen formulations, provide excellent UV protection and have a high SPF rating. Moreover, micronised, insoluble organic UV absorbers show no tendency, under the influence of light, to generate radicals which could damage or sensitise human skin.

The particle size of micronized organic UV absorbers is a critical parameter. Micronized organic compounds are effectful UV absorbers in the nanoscalar range which is <120 nm. With conventional grinding technologies using SAZ ceramic grinding beads these small particle sizes can only be achieved with a high energy input which is usually more than 5 kWh/kg starting from an aqueous dispersion comprising the micronized organic UV absorber.

Surprisingly it has been found that micronized organic UV absorbers in the nanoscalar range<120 nm can be obtained with a moderate energy input by a grinding method using yttrium-stabilized zirconium oxide grinding beads.

Therefore, the present invention relates to a method of preparing a composition, comprising a micronised insoluble organic UV absorber, which method comprises grinding the insoluble organic UV absorber, in coarse particle form, in a grinding apparatus comprising yttrium-stabilized zirconium oxide grinding beads in the presence of an antifoam agent as dispersing agent auxiliary.

Preferably the micronised insoluble organic UV absorber is selected from the compounds of formula

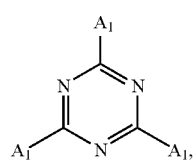
(1)

wherein
A is a radical of formula

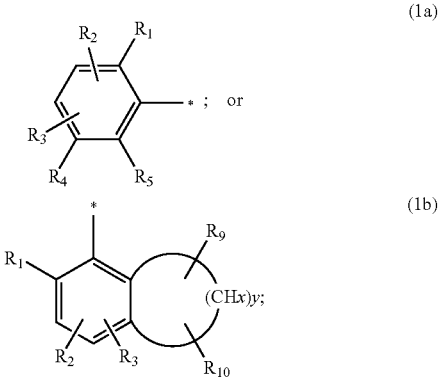

$R_1$ and $R_5$ independently from each other are hydrogen; $C_1$-$C_{18}$alkyl; or $C_6$-$C_{12}$aryl;
$R_2$, $R_3$ and $R_4$ independently from each other are hydrogen; or a radical of formula

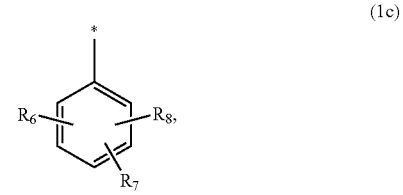

wherein at least one of the radicals $R_2$, $R_3$ and $R_4$ are a radical of formula (1c);
$R_6$, $R_7$, $R_8$, $R_9$ and $R_{10}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; —COOH;
M is an alkali metal ion;
x is 1 or 2; and
y is a number from 2 to 10.

More preferably the insoluble UV absorber is selected from the compounds of formula

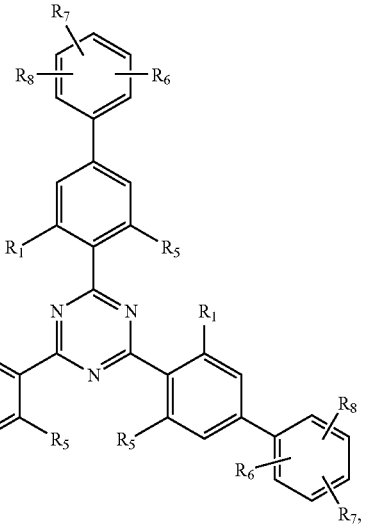
(2)

wherein
$R_1$, $R_5$, $R_6$, $R_7$ and $R_8$ are defined as in formula (1), and preferably $R_1$ and $R_5$ are hydrogen.

Preferably in formulas (1) and (2) $R_6$ and $R_8$ are hydrogen; and $R_7$ is hydrogen; hydroxy; $C_1$-$C_5$alkyl; $C_1$-$C_5$alkoxy; —COOM; —COOH; or $COOR_{10}$;

M is an alkali metal ion; and $R_{10}$ is $C_1$-$C_5$alkyl.

Most preferred in the method of the present invention are the compounds of formula

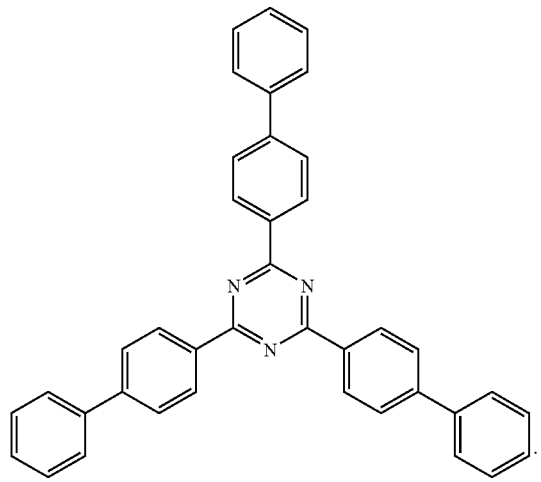

(3)

Furthermore, the micronized insoluble UV absorber used in the present invention is selected from the compounds of formula

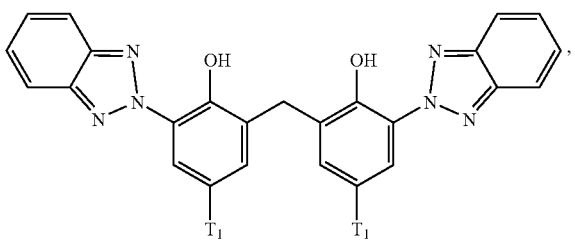

(4)

wherein $T_1$ is $C_1$-$C_{18}$alkyl, which is optionally substituted by phenyl; and more preferably $C_1$-$C_8$alkyl.

Most preferred are the micronized UV absorbers of formula

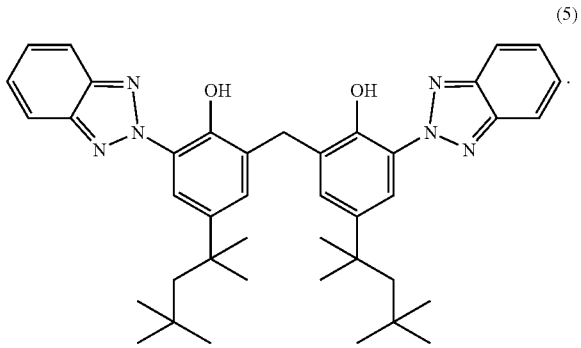 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]

(5)

Furthermore, the micronized insoluble UV absorber used in the present invention is selected from the compounds of formula

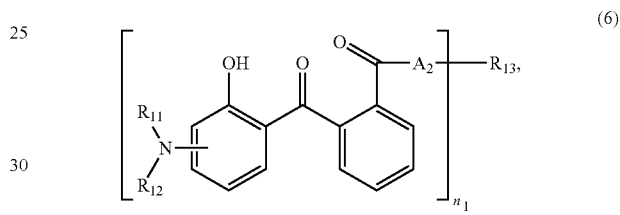

(6)

wherein $R_{11}$ and $R_{12}$ independently from each other are $C_1$-$C_{20}$alkyl; $C_2$-$C_{20}$alkenyl; $C_3$-$C_{10}$cycloalkyl; $C_3$-$C_{10}$cycloalkenyl; or $R_{11}$ and $R_{12}$ together with the linking nitrogen atom form a 5- or 6-membered heterocyclic ring;

$n_1$ is a number from 1 to 4;

when $n_1=1$, $R_{13}$ is a saturated or unsaturated heterocyclic radical; hydroxy-$C_1$-$C_5$alkyl; cyclohexyl optionally substituted with one or more $C_1$-$C_5$alkyl; phenyl optionally substituted with a heterocyclic radical, aminocarbonyl or $C_1$-$C_5$alkylcarboxy;

when $n_1$ is 2, $R_{13}$ is an alkylene-, cycloalkylene, alkenylene or phenylene radical which is optionally substituted by a carbonyl- or carboxy group; a radical of formula *—$CH_2$—C≡C—$CH_2$—* or $R_{13}$ together with $A_2$ forms a bivalent radical of the formula

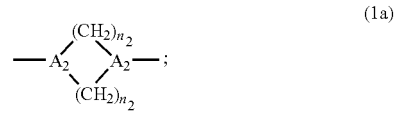

(1a)

$n_2$ is a number from 1 to 3;

when $n_1$ is 3, $R_{13}$ is an alkantriyl radical;

wenn $n_1$ is 4, $R_{13}$ is an alkantetrayl radical;

$A_2$ is —O—; or —N($R_{15}$)—; and $R_{15}$ is hydrogen; $C_1$-$C_5$alkyl; or hydroxy-$C_1$-$C_5$alkyl.

Most preferred in the method of the present invention is the micronized insoluble UV absorber of the formula

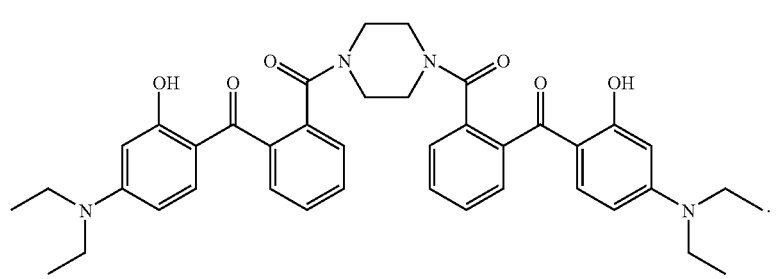

(7)

$C_1$-$C_{20}$alkyl denotes a linear or branched, unsubstituted or substituted alkyl group such as, for example, methyl, ethyl, propyl, isopropyl, n-butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxy-ethyl, 3-(2,4-di-tert-amylphenoxy)-propyl, ethoxycarbonylmethyl-2-(2-hydroxyethoxy)ethyl or 2-furylethyl.

$C_2$-$C_{20}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_3$-$C_{10}$cycloalkyl is for example cyclopropyl, cyclobutyl, cyclopentyl, cycloheptyl, cyclooctyl, cyclononyl or cyclodecyl and preferably cyclohexyl. These radicals may besubstituted, for example by one or more or equal or different $C_1$-$C_4$alkyl radicals, preferably by methyl, and/or hydroxy. If cycloalkyl radicals are substituted by one or more radicals, they are preferably substituted by one, two or four, preferably by one or two equal or radicals.

$C_3$-$C_{10}$cycloalkenyl is for example cyclopropenyl, cyclobutenyl, cyclopentenyl, cycloheptenyl, cyclooncentyl, cyclononenyl or cyclodecenyl and preferably cyclohexenyl. These radicals may be substituted with one or more equal or different $C_1$-$C_4$alkyl radical, preferably with methyl, and/or hydroxy. If cycloalkenyl radicals are substituted with one, or more radicals they are preferably substituted with one, two, three or four, preferably with one or two equal or different radicals.

Hydroxy-substituted $C_1$-$C_5$alkyl groups are for example hydroxymethyl, hydroxyethyl, hydroxypropyl, hydroxybutyl or hydroxypentyl.

An alklyene radical is preferably a $C_1$-$C_{12}$alkylene radical, like for example methylene, ethylene, propylene, butylene, hexylene or octylene.

The alklyene radicals may optionally be substituted by one or more $C_1$-$C_5$alkyl radicals.

If $R_1$ and $R_2$ are heterocyclic radicals, these comprise one, two, three or four equal or different ring hetero atoms. Special preference is given to heterocycles which contain one, two or three, especially one or two, identical or different hetero atoms. The heterocycles may be mono- or poly-cyclic, for example mono-, bi- or tri-cyclic. They are preferably mono- or bi-cyclic, especially monocyclic. The rings preferably contain 5, 6 or 7 ring members. Examples of monocyclic and bicyclic heterocyclic systems from which radicals occurring in the compounds of formula (1) or (2) may be derived are, for example, pyrrole, furan, thiophene, imidazole, pyrazole, 1,2,3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothio-phene, benzofuran, pyrrolidine, piperidine, piperazine, morpholine and thiomorpholine.

The yttrium-stabilized zirconium oxide grinding beads used in the present invention is a high density, highly spherical product that is predestinated for horizontal mills. It's density (>6 g/cc) makes it capable for high viscosity mill bases.

Furthermore, the yttrium-stabilized zirconium oxide grinding beads do not oxidize ("rust") in the presence of aqueous dispersions. As a result, they offer the advantages of the density of metallic media without the oxidation.

Typical yttrium-stabilized zirconium oxide grinding beads have the following properties:

| | |
|---|---|
| Chemical Composition | 95% $ZrO_2$, 5% $Y_2O_3$ |
| Specific Density: | 6.0 g/cm$^3$ |
| Bending Strength: | 1200 MPa |
| Hardness (Hv10): | 1250 |
| Modulus of Elasticity: | 210 GPa |
| Fracture Toughness: | 6.0 MPam$^0$ |

The sparingly soluble organic compounds which are used in the present invention are present in the micronized state and are preferably prepared by wet-milling processes.

As milling apparatus for the preparation of the sparingly soluble micronised organic compounds there may be used, for example, a jet mill, ball mill, vibratory mill or hammer mill, preferably a high-speed mixing mill. Even more preferable mills are modern ball mills; manufacturers of these types of mill are, for example, Netzsch (LMZ mill), Drais (DCP-Viscoflow or Cosmo), Bühler AG (centrifugal mills) or Bachhofer.

The insoluble organic UV absorbers used in the present invention are preferably micronized in the presence of an alkyl polyglucoside. Moreover, such formulations do not agglomerate and they remain in a dispersed form and do not readily settle.

The grinding of the sparingly soluble organic compounds used in the present invention is preferably carried out with an antifoam agent as grinding aid.

The antifoam agent is preferably selected from carrier oils, silicone oils and silicone foam inhibitors, hydrophobic silica, hydrophobic fat dervatives and waxes, water-insoluble polymers, amphiphilic components, emulsifiers and coupling agents.

Carrier oils are water-insoluble paraffinic and naphthenic mineral oils, together with vegetable oils such as tall oil, castor oil, soybean oil or peanut oil. Useful agents include residues from the oxo alcohol synthesis, alkylbenzenes, and rude oils from the low-temperature carbonization of brown coal or other bituminous materials.

The most important silicone oils are the polydimethylsiloxanes, in which chain ends are saturated with trimethylsilyl groups. The number of siloxane units represents ranges typically from 2 to 2000.

Silicon antifoam agents are supplied in the form of anhydrous dispersions of pyrogenic or hydrophobized silica in silicone oil. Such mixtures are oily and cloudy. In some cases they have the consistency of a paste, but the most commonly used foam inhibitors for aqueous systems are 5-50% emulsions.

Further examples of antifoam agents which may be used in the present invention are hydrophobic silica. Several methods have been perfected for the preparation of hydrophobic silica. The most important are spraying the silica with silicone oil and tempering at 250-350° C., treatment with organosilicon halide vapors in an autoclave, and dispersing the silica in a silicone oil at elevated temperature and recovery of the solid by centrifugation.

Hydrophobic fat derivatives and waxes include the following materials:
  fatty acid esters of monofunctional and polyfunctional alcohols;
  fatty acid amides and sulfonamides;
  paraffinic hydrocarbon waxes, ozokerite, and montan wax;
  phosphoric acid mono-, di-, and triesters of short- and long-chain fatty alcohols;
  short- and long-chain natural or synthetic fatty alcohols;
  water-insoluble soaps of long-chain fatty acids, including aluminum stearate, calcium stearate, and calcium behenate;
  perfluorinated fatty alcohols.

Examples for water-insoluble polymers are low molecular mass, fatty acid modified alkyl resins; low molecular mass novolaks; copolymers of vinyl acetate and long-chain maleic and fumaric acid diesters; and methyl mthacrylate-vinylpyrrolidone polymers. Other relevant polymeric materials include poly(propylene glycols) and high molecular mass propylene oxide adducts of glycerol, trimethylpropane, pentaerythritol, triethanolamine, dipentaerythritol or polyglycerol, addition products of butylene oxide or long-chain α-epoxides with polyvalent alcohols.

Amphiphilic compounds include antifoam components with varying water solubility whose foam-inhibiting effects are due to a variety of mechanisms. Examples include sodium oleate and the hardened fish fatty acid soaps used as foam regulators in detergents, nonionic surfactants as modestly ethoxylated alcohols, fatty acids, rosin acids, fatty amines and alkyl-phenol derivatives with HLB (Hydrophilic-Lipophilic Balance) values <10. Further examples are silicon surfactants. These are silicone oils to which polyether groups have been chemically bonded.

Examples for emulsifiers are ethoxylated sorbitan esters.

Examples for coupling agents are glycols, low molecular mass alcohols or other ingredients known as solublizers such as naphthalenesulfonate or p-toluenesulfonate.

The anti-foam agents are used in amounts from 0.01 to 10, preferably from 0.01 to 1% b.w., based on the micronized UV absorber dispersion.

Preferably, the micronised insoluble organic UV absorber, produced according to the method of the present invention, has a mean particle size in the range of from 0.01 to 2, more preferably from 0.02 to 1.5, especially from 0.05 to 1.0μ.

Most preferably, the mean particle size is in the range of from 0.01 to 2.0μ.

The compounds of the formula (1) prepared according to the method according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations.

The cosmetic formulations or pharmaceutical compositions according to the present invention may additionally contain one or more than one further conventional UV filter as listed in Table 1 below:

TABLE 1

Suitable UV filter substances and adjuvants which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts (Mexoryl SL) | 56039-58-8 |
| 11 | 1-[4-(1,1-dimethylethyl)phenyl]-3-(4-methoxyphenyl)propane-1,3-dione (Avobenzone) | 70356-09-1 |
| 12 | Methyl N,N,N-trimethyl-4-[(4,7,7-trimethyl-3-oxobicyclo[2,2,1]hept-2-ylidene)methyl]anilinium sulphate (Mexoryl SO) | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; octocrylene | 6197-30-4 |
| 30 | 2-ethylhexyl 4-(dimethylamino)benzoate | 21245-02-3 |
| 31 | 2-ethylhexyl 4-methoxycinnamate; octyl methoxy cinnamate | 5466-77-3 |
| 32 | 2-ethylhexyl salicylate | 118-60-5 |

TABLE 1-continued

Suitable UV filter substances and adjuvants which can be additionally used with the UV absorbers according to the present invention

| No. | Chemical Name | CAS No. |
|---|---|---|
| 33 | Benzoic acid, 4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine (Octyl Triazone) | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid] (Cibafast H) | 90457-82-2 |
| 42 | Titanium dioxide (primary particle size 10-50 nm) For example T805 or Eusolex T-AVO, Eusolex T-2000, Titaniumdioxid VT 817 | 13463-67-7 |
| 44 | Zinc oxide (primary particle size 20-100 nm) For example Zinc oxide NDM, Zinc oxide Z-Cote HP1, Nanox Zinc oxide | 1314-13-2 |
| 45 | 2,2'-Methylene-bis-[6-(2H-benzotriazol-2-yl)-4-(1,1,3,3-tetramethyl-butyl)-phenol] (Tinosorb M) | 103597-45-1 |
| 46 | 2,4-bis{[4-(2-ethylhexyloxy)-2-hydroxy]-phenyl}-6-(4-methoxyphe-nyl)-(1,3,5)-triazine (Tinosorb S) | 187393-00-6 |
| 47 | 1H-Benzimidazole-4,6-disulfonic acid, 2,2'-(1,4-phenylene)bis-, di-sodium salt | 180898-37-7 |
| 48 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester; diethylhexyl butamido triazone (Uvasorb HEB) | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane (Mexoryl XL) | 155633-54-8 |
| 50 | Dimethicodiethylbenzalmalonate; Polysilicone 15 (Parsol SLX) | 207574-74-1 |
| 51 | Benzenesulfonic acid, 3-(2H-benzotriazol-2-yl)-4-hydroxy-5-(1-methylpropyl)-, monosodium salt (Tinogard HS) | 92484-48-5 |
| 52 | Benzoic acid, 2-[4-(diethylamino)-2-hydroxybenzoyl]-, hexyl ester (Uvinul A Plus) | 302776-68-7 |
| 53 | 1-Dodecanaminium, N-[3-[[4-(dimethylamino)benzoyl]amino]propyl]-N,N-dimethyl-, salt with 4-methylbenzenesulfonic acid (1:1) (Escalol HP610) | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetrial, 1-(4-aminobenzoate) (Glyceryl PABA) | 136-44-7 |
| 62 | Benzeneacetic acid, 3,4-dimethoxy-a-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetra-sulfonate (Neo Heliopan AP) | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- (Uvasorb K2A) | 288254-16-0 |
| 67 | Merocyanine derivatives as described in WO 2004006878, WO2006032741, IPCOM000022279D and in IP.COM JOURNAL (2005), 5(7B), 18 | |

68

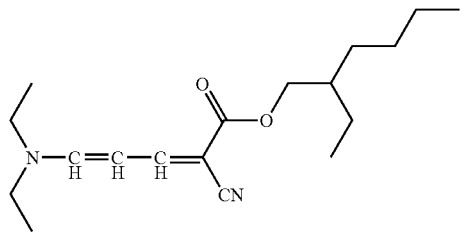 [SMILES: CCCCC(CC)COC(=O)C(C#N)=CC=CN(CC)CC]

69 sterols (cholesterol, lanosterol, phytosterols), as described in WO0341675

TABLE 1-continued

Suitable UV filter substances and adjuvants which can be additionally used with the UV absorbers according to the present invention

| No. | Chemical Name | CAS No. |
|---|---|---|
| 70 | mycosporines and/or nycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 71 | alpha-lipoic-acid as described in DE 10229995 | |
| 72 | synthetic organic polymers as described in EP 1371358, [0033]-[0041] | |
| 73 | phyllosilicates as described in EP 1371357 [0034]-[0037] | |
| 74 | silica compounds as described in EP1371356, [0033]-[0041] | |
| 75 | inorganic particles as described in DE10138496 [0043]-[0055] | |
| 76 | latex particles as described in DE10138496 [0027]-[0040] | |
| 77 | 1H-Benzimidazole-4,6-disulfonic acid, 2,2'-(1,4-phenylene)bis-, disodium salt; Bisimidazylate (Neo Heliopan APC) | 180898-37-7 |
| 78 | [structure] | |
| 79 | [structure] | |
| 80 | [structure] E or Z isomer or mixture of E/Z isomers | |
| 81 | [structure] | |
| 82 | Di-2-ethylhexyl-3,5-dimethoxy-4-hydroxy-benzalmalonate (Oxynex ST, EMD Chemicals, as described in US 20040247536) | |
| 83 | 2,4,6-Tris-1,1',4',1''-terphenyl-4-yl-1,3,5-triazine | |
| 84 | 2,4,6-Tris(p-biphenylyl)-s-triazine | 31274-51-8 |

The cosmetic or pharmaceutical preparations may be, for example, creams, gels, lotions, alcoholic and aqueous/alcoholic solutions, emulsions, wax/fat compositions, stick preparations, powders or ointments. In addition to the above-mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, esters of fatty acids, natural or synthetic triglycerides including glyceryl esters and derivatives, pearlescent waxes:hydrocarbon oils: silicones or siloxanes, organosubstituted super-fatting agents, surfactantsconsistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, polymeric beads or hollow spheres as spf enhancers.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber composition according to the invention, 12.0% by weight of sodium laureth-2-sulfate, 4.0% by weight of cocamidopropyl betaine, 3.0% by weight of sodium chloride, and water ad 100%.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, anti-oxidants, anti-irritants and anti-inflammatory agents etc.

The cosmetic preparation according to the invention is distinguished by excellent protection of human skin against the damaging effect of sunlight.

EXAMPLES

A. Preparation Examples

Example A1

The grinding formulation comprises as UV absorber tris-biphenyl-triazine and 1% of simethicone, which is a a mixture of Dimethicone with an average chain length of 200 to 350 dimethylsiloxane units and hydrated silica.

Grinding Formulation

| % | Ingredient | INCI/chemical name |
|---|---|---|
| 50 | UV absorber | Tris-biphenyl Triazine |
| 39.6 | Water | Aqua/Water |
| 1.3 | Caustic soda solution 1 mol/l | Sodium Hydroxide |
| 7.5 | Plantacare 2000 UP | Decyl glucoside |
| 1 | Silfoam SE 2 (corresp. 0.2% Simethicone) | Polydimethylsiloxane + Filler |
| 0.3 | Disodium hydrogen phosphate | Disodium hydrogen phosphate |
| 0.2 | Butylene glycol | 1,3 Butandiol |
| 0.1 | Rhodia Xanthan Gum | Xanthan gum |

The grinding is carried out in a Bachhofen-pilot-mill having a grinding container of 0.6 liters. Grinding aggregates are accelerators (whell-like grinding aggregates) from Bachhofen.

Grinding beads are yttrium-stabilized zirconium oxide (draison perarls from Tosoh) with an average particle size of 0.3-0.4 mm.

The Grinding beads filling is 65 to 70% b.w. of the grindingspace volumn.

The stirring speed is 8 m/s over 15 minutes, with water cooling.

The grinding aids are centrifuged off after the milling process.

Example A2

The yttrium-stabilized zirconium oxide grinding beads of Example A1 are substituted by SAZ grinding pearls ER120, size 0.3 to 0.4 mm and accelerators are made of yttrium-stabilized zirconium oxide.

Example A3

The accelerators of Example A2 are replaced by steel accelerators.

Measurements

Particle sizes are determined with FOQELS.

Extinction is calculated on 1 cm at 1% based on the active Tris-biphenyl Triazine, measured in a 8 μm sandwich cuvette (Hellma) in a Perkin-Elmer UV-Vis spectrometer with an integration ball at an active concentration of ca. 1%.

Results

| | Application of energy [kWh/kg dispersion] | E 1, 1 | Particle size $D_{50}/D_{90}$ [nm] |
|---|---|---|---|
| Example A1 | 1.8 | 1230 | 88/180 |
| Example A2 | 2.8 | 1180 | 95/200 |
| Example A3 | 2.2 | 1190 | 95/190 |

The invention claimed is:

1. A method of preparing a composition, comprising a micronised insoluble organic UV absorber with a mean particle size <0.1 μ, which method comprises grinding the insoluble organic UV absorber, in coarse particle form, in a grinding apparatus comprising yttrium-stabilized zirconium oxide grinding beads, in the presence of alkyl polyglucoside having the formula $C_nH_{2n+1}O(C_6H_{10}O_5)_xH$, in which n is an integer ranging from 8 to 16 and x is the mean polymerisation level of the glucoside moiety $(C_6H_{10}O_5)$ and ranges from 1.4 to 1.6, or an ester thereof and in the presence of an antifoam agent as dispersing agent auxiliary.

2. A method according to claim 1, wherein the micronised insoluble organic UV absorber is selected from the compounds of formula (1)

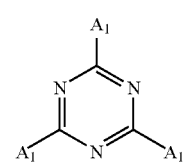

(1)

wherein
A is a radical of formula

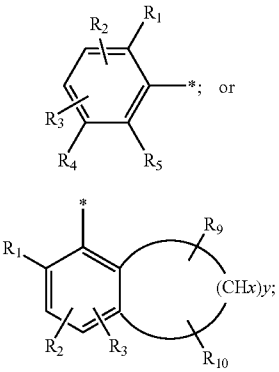
(1a)

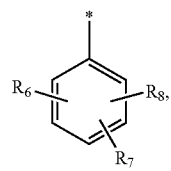
(1b)

$R_1$ and $R_5$ independently from each other are hydrogen; $C_1$-$C_{18}$alkyl; or $C_6$-$C_{12}$aryl;

$R_2$, $R_3$ and $R_4$ independently from each other are hydrogen; or a radical of formula (1c)

wherein at least one of the radicals $R_2$, $R_3$ and $R_4$ are a radical of formula (1C);

$R_6$, $R_7$, $R_8$, $R_9$ and $R_{10}$ independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; mono- or di-$C_1$-$C_{18}$alkylamino; $C_1$-$C_{10}$acylamino; or —COOH;

M is an alkali metal ion;

X is 1 or 2; and y is a number from 2 to 10.

3. A method according to claim 2, wherein the micronized insoluble UV absorber is selected from compounds of formula (2)

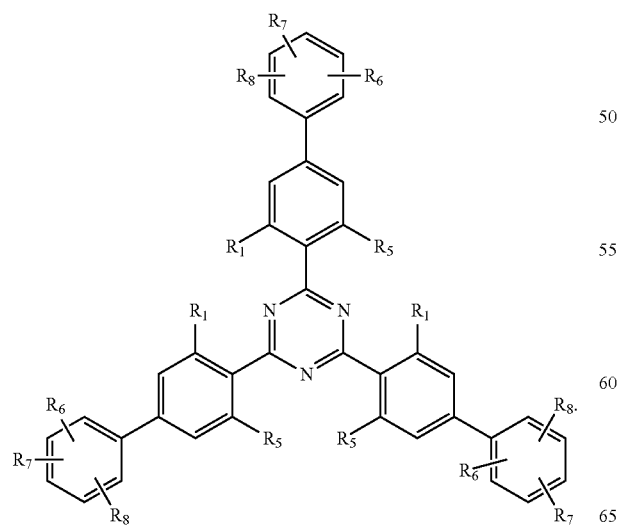
(2)

4. A method according to claim 3, wherein $R_1$ and $R_5$ are hydrogen.

5. A method according to claim 4, wherein $R_6$ and $R_8$ are hydrogen.

6. A method according to claim 5, wherein $R_7$ is hydrogen; hydroxy; $C_1$-$C_5$alkyl; $C_1$-$C_5$alkoxy; —COOM; —COOH; or COOR$_{10}$;

M is an alkali metal ion; and $R_{10}$ is $C_1$-$C_5$alkyl.

7. A method according to claim 6, wherein the insoluble UV absorber is of formula (3)

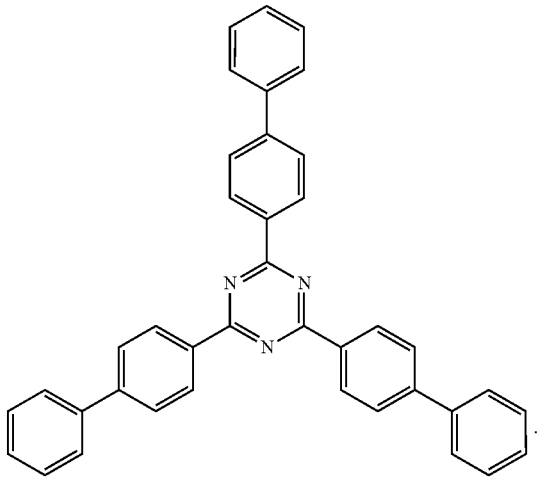
(3)

8. A method according to claim 1, wherein the micronized insoluble UV absorber is selected from compounds of formula (4)

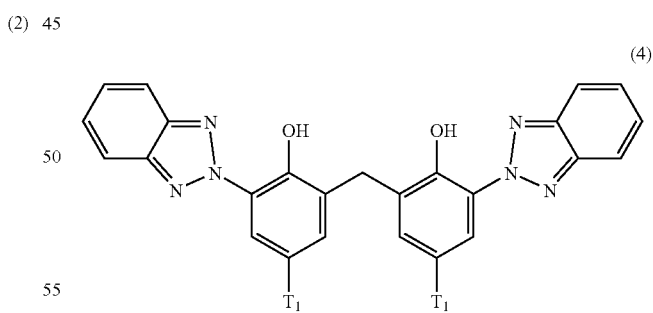
(4)

wherein
$T_1$ is $C_1$-$C_{18}$alkyl, which is optionally substituted by phenyl.

9. A method according to claim 8, wherein
$T_1$ is $C_1$-$C_8$alkyl.

10. A method according to claim 9, wherein the micronized insoluble UV absorber corresponds to formula (5)

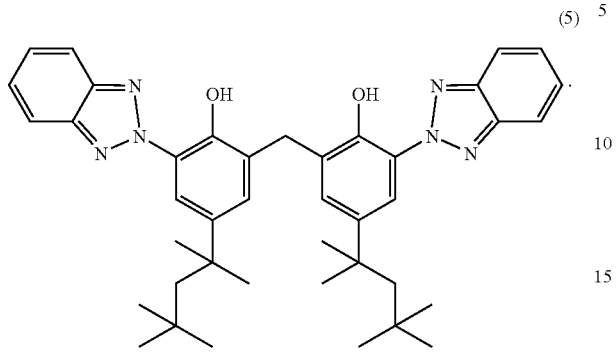
(5)

11. A method according to claim 1, wherein the micronized insoluble UV absorber is selected from compounds of formula (6)

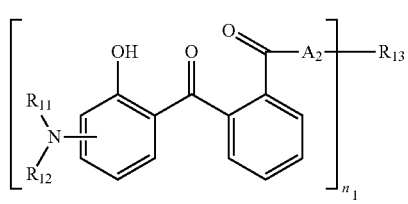
(6)

wherein
$R_{11}$ and $R_{12}$ independently from each other are $C_1$-$C_{20}$alkyl; $C_2$-$C_{20}$alkenyl; $C_3$-$C_{10}$cycloalkyl; $C_3$-$C_{10}$cycloalkenyl; or $R_{11}$ and $R_{12}$ together with the linking nitrogen atom form a 5- or 6-membered heterocyclic ring;
$n_1$ is a number from 1 to 4;
when $n_1$=1,
$R_{13}$ is a saturated or unsaturated heterocyclic radical; hydroxy-$C_1$-$C_5$alkyl; cyclohexyl optionally substituted with one or more $C_1$-$C_5$alkyl; or is phenyl optionally substituted with a heterocyclic radical, aminocarbonyl or $C_1$-$C_5$alkylcarboxy;
when $n_1$ is 2,
$R_{13}$ is an alkylene-, cycloalkylene, alkenylene or phenylene radical which is optionally substituted by a carbonyl- or carboxy group; a radical of formula *—$CH_2$—C≡C—$CH_2$—* or $R_{13}$ together with $A_2$ forms a
bivalent radical of the formula

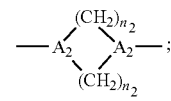
(1a)

wherein
$n_2$ is a number from 1 to 3;
when $n_1$ is 3,
$R_{13}$ is an alkantriyl radical;
when $n_1$ is 4,
$R_{13}$ is an alkantetrayl radical;
$A_2$ is —O—; or —N($R_{15}$)—; and
$R_{15}$ is hydrogen; $C_1$-$C_5$alkyl; or hydroxy-$C_1$-$C_5$alkyl.

12. A method according to claim 11, wherein the micronized insoluble UV absorber corresponds to formula (7)

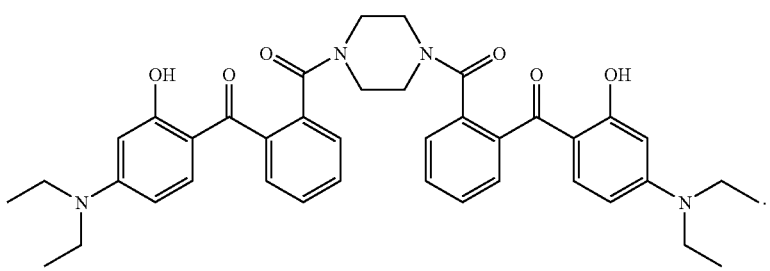
(7)

13. A method according to claim 1 in which the antifoam agent is selected from carrier oils, silicone oils, silicone foam inhibitors, hydrophobic silica, hydrophobic fat dervatives, waxes, water-insoluble polymers, amphiphilic components, emulsifiers and coupling agents.

14. A method according to claim 13, wherein the antifoam agent is selected from polydimethylsiloxane.

15. A method according to claim 1 in which the amount of antifoam agent is from 0.01 to 1% b.w.

* * * * *